United States Patent [19]

Thistle et al.

[11] Patent Number: 4,758,596

[45] Date of Patent: Jul. 19, 1988

[54] METHOD FOR THERAPEUTIC USE OF METHYL TERTIARY-BUTYL ETHER

[75] Inventors: Johnson L. Thistle, Rochester, Minn.; Mark J. Allen, Kansas City, Mo.

[73] Assignee: Research Corporation, New York, N.Y.

[21] Appl. No.: 649,389

[22] Filed: Sep. 11, 1984

Related U.S. Application Data

[63] Continuation-in-part of Ser. No. 599,398, Apr. 10, 1984.

[51] Int. Cl.$^4$ .............................................. A61K 31/08
[52] U.S. Cl. ..................................... 514/722; 514/877; 604/48
[58] Field of Search .................. 604/48; 568/671, 697; 514/722, 877

[56] References Cited

U.S. PATENT DOCUMENTS

| 1,846,596 | 2/1932 | Hertzberg | 604/30 |
|---|---|---|---|
| 2,024,967 | 12/1935 | Dierker | 604/30 |
| 3,042,041 | 7/1962 | Jascalevich | 604/276 |
| 3,142,299 | 7/1964 | Henderson | 604/38 |
| 3,316,910 | 5/1967 | Davis | 604/28 |
| 3,329,147 | 7/1967 | Barron | 604/151 |
| 3,426,743 | 2/1969 | Chestnut et al. | 604/66 |
| 3,429,313 | 2/1969 | Romanelli | 604/35 |
| 3,885,567 | 5/1975 | Ross | 604/151 |
| 3,888,994 | 6/1986 | Wagner et al. | 514/723 |
| 3,892,226 | 7/1975 | Rosen | 604/37 |
| 3,955,574 | 5/1976 | Rubinstein | 604/151 |
| 4,041,947 | 8/1977 | Weiss et al. | 604/51 |
| 4,205,086 | 5/1980 | Babayan | 514/877 |
| 4,205,176 | 5/1980 | Zestermann et al. | 548/239 |
| 4,255,096 | 3/1981 | Coker et al. | 604/152 |
| 4,282,873 | 8/1981 | Roth | 604/37 |
| 4,315,506 | 2/1982 | Kayser et al. | 604/35 |
| 4,447,226 | 5/1984 | Mayoral | 604/32 |
| 4,457,755 | 7/1984 | Wilson | 604/38 |
| 4,464,399 | 8/1984 | Hofmann | 514/877 |
| 4,516,398 | 5/1986 | Wuchinich | 604/35 |
| 4,525,156 | 6/1985 | Benusa et al. | 604/32 |
| 4,526,575 | 7/1985 | Roblejo | 604/54 |

FOREIGN PATENT DOCUMENTS 2944782 5/1981 Fed. Rep. of Germany .

OTHER PUBLICATIONS

Buglios; T. F. et al., "Methyl Tertiary-Butyl Ether (MTBE) in Expired Air and Methanol in Blood Do Not Reach Potentially Harmful Levels After Gallbladder and Duodenal Instillation of Therapeutic Doses of MTBE in Dogs", Gastroenterology-vol. 86(5), Part 2, May 1984, p. 1313.
Buglios; T. F. et al.-"Rapid Gallstone Dissolution in Dogs Using Methyl Tertiary-Butyl Ether and an Aspiration-Infusion Pump", Gastroenterology-vol. 86 (5), Part 2, May 1984, p. 1350.
The Merck Index, 10th Ed. (1983), pub. by Merck & Co., Rahway, N.J., pp. 865-866, Item 5908, Methyl Tertiary Butyl Ether.
Allen, M. J. et al., "Rapid Dissolution of Gallstones by Methyl Tert-Butyl Ether", The New England Journal of Medicine, vol. 312, No. 4, Jan. 24, 1985, pp. 217-220.
Allen, M. J. et al., "Cholelitholysis Using Methyl Tertiary Butyl Ether", Gastroenterology, vol. 88 (1985), pp. 122-125.
Y. Takasawa et al., "A Study on the Dissolution and Disintegration of Calcium Bilirubinate Stones, with Special Reference to Effects of Litholytic Agents in Human Bile and to Irrigation of Bile Duct in Dogs", Tohoku J., Exp. Med., 1982, 138, 383-395.
U. Leuschner et al., "Alternating Treatment of Common Bile Duct Stones with a Modified Glyceryl-1-Monooctanoate Preparation and a Bile Acid-EDTA Solution by Masobiliary Tube", Scand. J. Gastroent., 1981, 16, 491-503.
U. Leuschner et al., "Gallstone Dissolution in the Biliary Tract: in Vitro Investigations on Inhabiting Factors and Special Dissolution Agents", American Journal of Gastroenterology, vol. 77, No. 4, 1982, 222-226.
U. Leuschner et al., "Biochemical and Morphological Investigations of the Toxicity of a Capmul Preparation and a Bile Salt-EDTA Solution in Patients with Bile Duct Stones", American Journal of Gastroenterology, vol. 77, No. 4, 1982, 222-226.
U. Leuschner et al., "Dissolution of Bileduct Stones", Letter to the Editor, The Lancet, Feb. 7, 1981, 336.
International Journal of Clinical Pharmacology, Therapy and Toxicology, vol. 21, No. 1, pp. 37-40 (1983).
International Journal of Clinical Pharmacology, Therapy and Toxicology, vol. 21, No. 2, pp. 95-97 (1985).
U. Leuschner et al., "The Dissolution of CBD Cholesterol and Pigment Stones with Methyl-Teritiary-Butyl-Ether (MTBE) in Vitro and in Vivo, Gastroenterology, vol. 88, No. 5, Parts 2, no year listed.
U. Leuschner et al., "Treatment of Bile Duct Stones by Combined Use of Endosceopy and Flushing Therapy", A/S/G/E, vol. 28, No. 2, 1982, p. 137.
U. Leuschner et al., "Dissolution of Black Pigment Stones (BPS) of the Gallbladder", Gastroentrerology, vol. 88, No. 5, Parts 2, no year listed.
U. Leuschner et al., "Our 10 Years' Experience in Gallstones Dissolution, (Comparison with the National Cooperative Gallstone Study (NCGS) and the Tokyo Cooperative Gallstone Study (TCGS), Japan)", no journal listed.
Hepatology, vol. 3, No. 5, p. 809 (1983).
International Journal of Clinical Pharmacology, Therapy and Toxicology, vol. 19, No. 6, pp. 273-274 (1981).
Br. F. Surg., vol. 68, pp. 203-308 (1981).
Comn, H. F.-Current Therapy 1 1981-p. 366.

Primary Examiner—Mark L. Bell
Attorney, Agent, or Firm—Scully, Scott, Murphy & Presser

[57] ABSTRACT

Method for dissolving cholesterol calculus in vitro or in vivo comprising contacting the cholesterol calculus with methyl tertiary-butyl ether.

14 Claims, No Drawings

METHOD FOR THERAPEUTIC USE OF METHYL TERTIARY-BUTYL ETHER

CROSS REFERENCE TO RELATED PATENT APPLICATIONS

This patent application is a continuation-in-part of U.S. patent application Ser. No. 599,398, filed Apr. 10, 1984.

FIELD OF THE INVENTION

This invention relates to a therapeutic use of methyl tertiary-butyl ether. More particularly, the invention relates to the application of methyl tertiary-butyl ether as a solvent for cholesterol calculi.

BACKGROUND OF THE INVENTION

Cholesterol calculi are concretions comprising generally at least 40% cholesterol which generally may develop in hollow organs or ducts within humans and animals. Examples of common cholesterol calculi are cholesterol biliary duct stones and gallstones in the gallbladder. The presence of these stones within the body presents numerous health problems as would be known to those skilled in the art.

Various methods exist for removing cholesterol calculi from the bodies of humans and animals including surgery or in vivo dissolution of a calculus by the introduction of solvents into the body area where the body calculus resides. The hazards and complications attributable to surgery are well known to those skilled in the art. Thus, the advantages of avoiding or mitigating treatment by surgery for this condition are obvious.

Dissolution of cholesterol calculis in vivo has been undertaken with limited success, however, prior to the present invention. Prior to the present invention monooctanoin (MO) has been the preferred agent for safe in vivo dissolution of cholesterol calculi in the biliary duct but has not been reported to be effective for stones in the gall bladder. The methods used for employing mono-octanoin to date for this purpose usually require 3 to 21 days of treatment. Recently it has been shown that the effectiveness of mono-octanoin as a cholesterol biliary duct stone solvent can be increased up to about four-fold by in vivo stirring or agitation and can be increased up to about 15-fold with the additional exclusion of bile, whereby the treatment time is reduced to about ⅓ to ¼ the time required for the prior treatment with MO. These results are described and explained in the present inventors co-pending U.S. patent application entitled, "In Vivo Method for Distributing and Stirring of Therapeutic Agents," Ser. No. 599,398, filed Apr. 10, 1984, as well as in abstracts of papers appearing in: *Gastroenterology*, Volume 84, No. 5, Part 2, Page 1090, 1983; *Hepatology*, Volume 3, No. 5, Abstract No. 44, Page 809, 1983. The entire disclosure of these references is incorporated herein by reference.

Although these techniques for using MO can reduce the time needed to dissolve biliary duct stones, the time required for such treatment is still relatively long, particularly when the stones are relatively large and/or are not too well positioned, in vivo, for such treatment.

Diethyl ether has a cholesterol solubilizing capacity similar to MO (13.7 g/100 cc vs. 11.7 g/100 cc) but dissolves cholesterol gallstones much more rapidly than does MO. Diethyl ether, however, immediately vaporizes at its boiling point of 34.5° C. and expands its volume 120-fold. It is thus not useful for in vivo purposes.

A need still exists, therefore, for therapeutic agents and solvents which can dissolve cholesterol calculi, in vivo, including biliary duct stones in a shorter period of time than that provided for by the use of MO.

The advantages which can be derived from the use of more effective and time efficient solvents for the in vivo dissolution of cholesterol calculi include a reduction of the patient's discomfort during the introduction of the solvent in vivo, which is often via a catheter or other needle-like structure, as well as a reduction in the time the patient may be exposed to the risk of infection or other possible deleterious side effects of a treatment of this type, as well as being subject to a shorter hospital stay.

SUMMARY OF THE INVENTION

It is an object of the present invention, therefore, to provide a liquid medicament and method for dissolving cholesterol calculi in vivo at a substantially faster rate than conventionally available solvents such as monooctanoin (MO).

To achieve the objects in accordance with the purposes of the present invention as embodied and broadly described herein, the invention comprises a method for dissolving cholesterol calculi by contacting the calculi with methyl tertiary-butyl ether (MTBE). In preferred embodiments of the invention, the cholesterol calculus of a patient is contacted with MTBE in vivo. In further preferred embodiments of the invention the cholesterol calculus of a patient can be contacted in vivo with agitation or stirring to facilitate distribution of the MTBE and dissolving of the cholesterol calculus while aspirating or otherwise removing bile. The present invention also relates to a medicament for dissolving cholesterol calculi comprising a therapeutically effective amount of methyl tertiary-butyl ether (MTBE). In preferred embodiments of the invention the cholesterol calculus dissolved is selected from the group consisting of biliary duct stones and gallstones in the gallbladder.

DETAILED DESCRIPTION OF THE PREFERRED EMBODIMENTS

Reference will now be made in detail to the preferred embodiments of the method of the invention.

In accordance with the invention, MTBE is an effective and time-efficient medicament for dissolving cholesterol calculi both in vitro and in vivo.

MTBE is structurally related to diethyl ether but MTBE remains liquid at body temperature because of its favorable boiling point of 55.2° C. MTBE is thus usable in vivo as a liquid.

Cholesterol calculi includes biliary duct stones and gallstones in the gallbladder as well as cholesterol calculi within the arterial systems such as cholesterol plaque. MTBE is especially effective in vivo because it requires a shorter contact time for dissolving the cholesterol calculi than do the conventional solvents such as mono-octanoin which have been employed for this purpose in the bilary tract. The use of MTBE thus significantly shortens the period of time needed for treatment of the patient.

In accordance with the method of the present invention then, the cholesterol calculi are rapidly dissolved by contacting the calculus with effective amounts of MTBE. The calculi may be dissolved both in vitro and in vivo.

The MTBE is used undiluted. An effective amount of MTBE, for the purposes of the present invention, is defined as that amount which when contacted with the cholesterol calculus, dissolves at least a significant portion of the cholesterol calculus. After a period of treatment time the MTBE solvent being used may become saturated with dissolved cholesterol calculus and have to be replaced with fresh MTBE to continue the treatment and obtain complete dissolution of the calculi.

The cholesterol calculi can be contacted in vivo with MTBE in a hollow duct, organ or arterial system of a patient. Methods for contacting the cholesterol calculi with MTBE in vivo include percutaneous transhepatic catheter placement (PTC); endoscopic retrograde biliary catheter placement; or placement of a catheter in a localized area by surgical means. The more particular areas of a patient's body wherein MTBE may be introduced for in vivo dissolving of cholesterol calculi include the biliary tract, gallbladder, and arteries of a patient.

As described in co-pending patent application Ser. No. 599,398, it has been found particularly effective, in employing the MBTE for the purposes contemplated herein, to employ the MTBE in an oscillating manner whereby the cholesterol calculi is contacted with oscillating MTBE and also subjected to stirring to facilitate the distribution of the MTBE at the site of the calculus and thus facilitate the dissolution of the calculus. It is also advantageous to provide a means for removing saturated MBTE and adding fresh or makeup MTBE to the site of the calculus in order to replenish the MTBE, or to replace any volume of MTBE which may be diminished by absorption into the body or otherwise.

A more specific description of the preferred embodiments of the invention is set out in the following Examples which relate to dissolving calculus material in a localized area of a patient's body. More particularly, the examples are concerned with the dissolution of gallstones by introducing MTBE in vivo to the localized area wherein the gallstones reside such as the biliary tract or the gallbladder and is demonstrated in both in vitro and in vivo trials. The Examples provide comparative data and results as shown in Table 1 below which illustrate the effectiveness of the medicament and method of the invention for dissolving cholesterol calculi versus conventional calculi solvents and medicaments.

Example 1, and Comparative Example 1, relate to the use of in vitro methods for dissolving gallstones.

EXAMPLE 1

Gall stones (90% cholesterol, 220–230 mg) from one human patient were placed in 5 cc of MTBE and subjected to gentle stirring. Stirring was continued until the gallstone was completely dissolved, which took one hour.

COMPARATIVE EXAMPLE 1

This comparative example was carried out according to the same method as Example 1 except that monooctanoin (MO) was used as a solvent in place of MTBE. Whereas the gallstone in the MTBE was dissolved within one hour, the MO solvent required from 52 to 56 hours to achieve complete lysis. The gallstones used in Comparative Example 1 were from the same human patient, and were of the same size, as those used in Example 1.

EXAMPLES 2 and 3

Examples 2 and 3 relate to in vivo examples of the methods of the invention carried out by dissolving human gallstones that had been implanted in dogs.

Methods

Each of nine (9) dogs had three (3) human gallstones and the pigtail end of a 5 Fr. polyvinyl catheter implanted into their gallbladders. All 27 stones were from the same patient. They were 94% cholesterol and were each 189–238 mg in weight. After a 10 day period of recovery from the implantation procedure, 3 groups of 3 dogs each of such dogs were then further treated as described in Examples 2 and 3 and Comparative Example 2.

EXAMPLE 2

Methyl tertiary butyl ether (MTBE) (20 ml) was instilled into the gallbladders of each of one set of three (3) of the dogs and then replaced hourly without stirring.

EXAMPLE 3

MTBE (20 ml) was instilled into the gallbladders of each of a second set of three (3) of the dogs and then continuous stirring was produced by alternate injection and aspiration of 5 ml MTBE in 30 second cycles.

COMPARATIVE EXAMPLE 2

MO (20 ml) was instilled into the gallbladder of each of a third set of three (3) of the dogs and stirring was performed using the same volume and cycle frequency as in Example 3. Stone size was determined every two hours by cholecystogram and complete dissolution confirmed by autopsy.

Stirring in Example 3 and Comparative Example 2 was accomplished by oscillating and agitating effective amounts of solvent with an alternating aspiration and infusion (injection) pump.

The volume range for aspiration and injection is adjustable from essentially 0 up to 15 cc. Both aspiration and injection volumes were identical. The rate of aspiration and injection were independently variable. The rate of injection could be independently adjusted from essentially 0 to a maximum injection of the full 15 cc within 4.8 seconds. The rate of aspiration can be independently set up to a maximum rate of aspiration of the full 15 cc over a period of 5 to 7 seconds. Since this is a continuous process, the number of aspiration-injection cycles per minute is dependent on the volumes and rates selected as well as the internal diameter of the lumen of the catheter used and the viscosity of the fluid. A very high level of continuous stirring (turbulence), however, can be accomplished within a wide range of conditions.

Table 1 below contains a comparison of the conditions used and results obtained in Examples 1 to 3 and in Comparative Examples 1 and 2.

TABLE 1

| Example | Stirring (in vitro) or Injecting and Aspirating (in vivo) | Solvent | Complete Stone Dissolution (hours) |
|---|---|---|---|
| 1 | Yes (in vitro) | MTBE | Less than 1 |
| Comp. 1 | Yes (in vitro) | MO | 54 ± 2 |
| 2 | No (in vivo) | MTBE | 11.3 ± 2.9 |
| Comp. 2 | Yes (in vivo) | MO | * |

| Example | Stirring (in vitro) or Injecting and Aspirating (in vivo) | Solvent | Complete Stone Dissolution (hours) |
|---|---|---|---|
| 3 | Yes (in vivo) | MBTE | 5.3 ± 0.7 |

*MO achieved only 33% stone dissolution after 60 hours even with stirring.

The results of the experiments shown in Table 1 illustrate the significant differences in utility, in vitro and in vivo, between MTBE and MO as a means for dissolving cholesterol calculi. MTBE provides significant improvements in treatment times.

EXAMPLE 4

In Vitro Studies

Sets of gallstones containing 94%, 40% and 0% cholesterol were obtained from three human patients. The cholesterol content of the stones were measured by the Zak-Ellefson method. Each stone was weighed, pulverized and dissolved in ether and isopropyl alcohol (1:1), and an aliquot of this solution was dried and resuspended in isopropyl alcohol. The cholesterol content of the dissolved stone was then measured colorimetrically (N. W. Tietz, Fundamentals of Clinical Chemistry, 2nd Edition, 1976, Chapter 10, pp. 514–516).

Single stones were separately placed in eight 5 cc wells all containing the same solvent, either MTBE or monooctanoin.

Each well was connected by an equal length of silastic tubing to a modified Filamatic pump (model AB), which gently stirred the stones every 2 seconds by alternate aspiration and infusion of 0.5 cc of the respective solvent. The stones were blotted dry before being weighed on an analytical balance, every ten minutes for MTBE, and every 6 to 12 hours for MO. Their weights were expressed as percent of the original weight. After weighing, the stones were returned to their wells until dissolution was complete. Mono-octanoin was replaced every 12 hours. MTBE was not replaced during the in vitro studies. All studies were carried out at 37° C.

The dissolution of the 94% cholesterol stones by MTBE was complete within one hour, while monooctanoin required 52–56 hours for such stones. The dissolution of the 40% cholesterol stones by MTBE was complete within 100 minutes, but MO required more than 50 hours to achieve complete dissolution of these stones. Pigment stones (0% cholesterol) were unaffected by either MTBE or mono-octanoin.

EXAMPLE 5

In Vivo Studies in Dogs

Fifteen human gallstones (90–94% cholesterol; 1–1.8 cm diameter) were surgically implanted into the gallbladders of six (6) female mongrel dogs weighing 15 to 20 kg each. Each dog received 2 or 3 stones. The pigtail end of a 5-Fr. pediatric nephrostomy catheter was sutured into the gallbladder fundus, while its proximal end was brought out through the abdominal wall, and connected to a metal flange for external access.

Seven to 10 days after surgery, MTBE was manually instilled into the gallbladder via the catheter in aliquots of 2–20 cc (x=15). The gallbladder was completely aspirated of both the solvent and accumulated bile at 30–60 minute intervals, and replaced with fresh solvent. The solvent was not otherwise stirred. Stone diameter was measured using serial cholecystograms. The extent of dissolution was confirmed at autopsy. Serum aminotransferase, alkaline phosphatase, bilirubin, amylase, lipase, creatinine and hemoglobin levels were determined pre and post treatment.

At autopsy, the gallbladder, common bile duct, duodenum, pancreas, liver, kidney, and lung were studied by light microscopy. Gallbladder mucosa was further examined by scanning electron microscopy.

Two further dogs underwent the procedure described above, each having three gallstones implanted in the gallbladder. However, no dissolution therapy was instituted in these dogs. After three and seven weeks their stones were removed and weighed.

Of the 15 gallstones implanted in the gallbladders of the dogs treated with MTBE, 14 dissolved completely after 4–16 hours of instillation of MTBE. The remaining stone was not seen radiologically after 8 hours and was thought to have dissolved entirely. Treatment was, therefore, stopped, but the stone, at 50% of its original weight, was discovered at autopsy.

Transient mild salivation and intermittent vomitting occurred in 4 of the 6 dogs, but no episodes of noticeable sedation occurred. No abnormalities were detected in serum levels of aminotransferase, bilirubin, amylase, lipase, creatinine or hemoglobin. A four-fold increase in serum alkaline phosphatase was noted in one of the six dogs and a two-fold increase in two others. At autopsy on gross inspection, a 3×4 mm area of minimal hemorrhage was seen close to the catheter tip in one of the 6 dogs. Upon examination on light microscopy, mild inflammatory changes consisting of round cell infiltration in submucosa and lamina propria were seen in all gallbladder specimens. Mild duodenitis was also noted in two dogs. No other histological abnormalities on light microscopy were seen in the common bile duct, liver, kidney, pancreas, lung or duodenum. Scanning electron micrographs were obtained on four of the six gallbladder specimens and revealed only minimal blunting of the microvilli.

In the two dogs not treated with MTBE, the implanted gallstones dissolved slowly, reaching 75% and 48% of their original weights when removed at three and seven weeks, respectively.

Based on the results of Examples 4 and 5, it is seen that, in vitro, methyl tertiary butyl ether dissolved the cholesterol gallstones 50 times faster than monooctanoin and was almost equally effective in dissolving stones containing 40% and 94% cholesterol. When used in vivo, the MTBE dissolved all but one of the 15 implanted gallstones within 16 hours. The weight of the remaining stone had been reduced by 50% after 8 hours when treatment was discontinued. Time required for total dissolution was longer in vivo than in vitro. A number of factors related to stone-solvent contact may have contributed to this difference. Gallstones sink in bile so that they rest in the most dependent part of the gallbladder. MTBE, in contrast, floats on bile. As bile accumulates in the gallbladder between MTBE instillations, it displaces the MTBE away from the stones. Stirring prevents this displacement and even in 100% MBTE in vitro stirring enhances the dissolution rate presumably by disrupting the unstirred solvent layer surrounding the stones.

Although dog bile can dissolve cholesterol gallstones, rates are in the order of weeks rather than hours. As noted above, when the same cholesterol gallstones used in the in vivo study were placed into the gallbladders of two untreated dogs, and the stones were removed at three and seven weeks, they were at 75% and 48% of their original weight, respectively.

The only clinical side effects observed were probable nausea, inferred from intermittent salivation, and occasional vomitting in 4 of the 6 treated dogs. This effect may have been mediated by a central mechanism similar to that seen with diethyl ether or due to biliary tract distension. Although MTBE is known to have anesthetic properties in other animal species, sedation was not observed, suggesting that little may have been absorbed from the gallbladder. Consistent with this impression, 80–90% of the instilled MTBE was recovered from the gallbladder 30 to 60 minutes after instillation.

With the exception of the serum alkaline phosphatase level, biochemical and hematologic parameters did not become abnormal during the study. In 2 of the 3 affected dogs, serum alkaline phosphatase rose following surgical implantation of the gallstones and catheter and then decreased during MTBE administration. Whether this biochemical abnormality is related to the surgical procedure, passage of stone fragments, or an inconsistent transient response to MTBE, per se, is not known at this time.

No histological evidence of hepatic, renal or pulmonary damage was found in these acute studies. Mild nonspecific inflammatory changes of gallbladder mucosa were present and could have resulted from the previous surgical procedure, catheter, gallstones, or the MTBE. The mild duodenitis on light microscopy seen in two dogs may have been caused by MTBE, although pretreatment tissue was not examined.

EXAMPLE 6

In Vivo Study In A Human Being

A 64-year old Caucasian female had an acute episode of steady upper abdominal pain and nausea in November 1983 which lasted three hours. The following month an oral cholecystogram demonstrated multiple radiolucent gallstones. In March 1984 she developed further episodes of midepigastric distress with nausea. She had an excessive fear of surgery yet desired rapid resolution of her symptoms. Therefore, she sought evaluation in May 1984 for consideration of nonoperative management of her cholelithiasis.

On physical examination her height was 161 cm and weight 84.8 kg. She was afebrile, pulse 72, and blood pressure 160/95 mm Hg. Her abdomen was obese but no masses, organomegaly, or tenderness were detected. Laboratory results revealed normal hematologic and biochemical parameters except for a serum gamma glutamyl transpepstidase of 131 (normal 6-35 u/l). An x-ray of the abdomen did not demonstrate calcification in her gallstones and a repeat oral cholecystogram again demonstrated normal opacification with multiple radiolucent gallstones. At endoscopy, a duodenal bile sample was obtained following cholecystokinin infusion and under both light and polarized light microscopy large numbers of typical cholesterol crystals together with a few aggregates of calcium bilirubinate were detected. Endoscopic examination was otherwise normal except for a small diaphragmatic hernia.

The patient was seen in surgical consultation and informed that cholecystectomy was the conventional treatment. She adamantly refused surgery yet expressed a strong desire for an alternative method which might rapidly dissolve her gallstones. The use of methyl tertiary butyl ether via a percutaneous transhepatic catheter was discussed in detail, and she strongly desired to be considered for this investigational approach. Informed consent was obtained.

A CT scan of the liver with contrast demonstrated a sufficient area of attachment of the gallbladder to the liver. Under sterile conditions using Lidocaine analgesia, a 21 guage Hawkins transhepatic cholangiographic needle was then placed via the hepatic-gallbladder bed into the gallbladder lumen. A wire guide was then inserted through the needle, the needle removed, and replaced by a 5 French pigtail catheter 40 cm in length. The catheter was specifically designed for this purpose having multiple lateral holes restricted to the pigtail end so as to provide maximum turbulence (Cook Catheter Company, Bloomington, IN). A bile sample was obtained for aerobic and anaerobic cultures and the biliary catheter was then connected to a closed system drainage bag.

The catheter was well tolerated overnight with no evidence of bleeding. The following morning repeat catheter cholangiogram demonstrated no evidence of extravasation. It was determined that only 12 ml of contrast media was required to fill the gallbladder which was otherwise nearly completely occupied by stones 1 to 1.5 cm in diameter. Infusion of 5 ml of contrast after maximal gallbladder aspiration, however, appeared to completely bathe all the stones. After aspiration of all contrast material, continuous infusion and aspiration of MTBE was begun. After aliquots of 1 ml were well tolerated, the volume was gradually increased during the following two hours to 5 ml. One-minute cycles of infusion and aspiration were performed to create uninterrupted stirring within the gallbladder. With each aspiration, bile was also withdrawn from the gallbladder. The syringe was kept dependent so that the heavier bile layered below the MTBE and was not reinfused. As bile accumulated in the syringes, they were replaced by fresh MTBE filled syringes so that only MTBE would be reinfused. Catheter cholangiograms were obtained at two, four, and seven hours of treatment.

Rapid, progressive stone dissolution was observed after two and four hours. After seven hours of treatment, no filling defects could be detected in any part of the biliary tree either after partial aspiration using dilute contrast medium or maximal filling. Real-time gallbladder ultrasonography demonstrated no intraluminal defects other than the catheter.

During rapid stone dissolution, the aspirated bile initially contained mahogany brown particles characteristic of calcium bilirubinate, and later developed the appearance of biliary "mud." During the final hour of treatment, the bile returned to its original light green color. As each syringe was exchanged, the volume of bile and MTBE was measured and stored in individual test tubes. In some aliquots obtained in the first two hours (during the period of most rapid stone dissolution) as the solvent cooled to room temperature, cholesterol crystallized in the MTBE reflecting its near saturation at body temperature.

MTBE has a disagreeable odor and can induce a dose-dependent nausea and vomitting similar to that caused by diethyl ether. During the treatment period, no odor of MTBE was detected on the patient's breath nor could she smell or taste it. She experienced no nausea, vomitting, somnolence, or other systemic symptoms. Since more than 90% of absorbed MTBE is rapidly exhaled and none could be detected on her breath, we concluded that very little was absorbed. Measured volumes of MTBE infused and then aspirated were similar, although a layer of emulsion at the bile-MTBE interface made this estimate inexact. Serum samples for analysis of MTBE and methanol, a minor metabolite of MTBE, were obtained immediately at the end of treatment. Serum MTBE did not exceed 10 ppm as determined by gas chromatography, and methanol was undetectable.

Following a normal catheter cholangiogram and ultrasound examination at the end of treatment, the catheter was removed over a guide wire without need for analgesia. After having a light liquid evening meal following catheter removal, the patient developed mild right upper quadrant discomfort. This was relieved by propoxyphene 65 mg. She remained afebrile and her hemoglobin remained unchanged at 14 g/dl. She developed a transient leukocytosis of 21,500 the day after catheter removal but this returned to normal within two days. Serum aminotransferases remained stable during therapy but following removal of the catheter became transiently elevated two- to three-fold. Three days after catheter removal her serum aminotransferase was 37 (normal to 31) and had returned completely to normal three days later.

Two days following completion of therapy and catheter removal, an oral cholecystogram demonstrated faint opacification despite a large amount of unabsorbed contrast media visible in the intestinal lumen. With Bilopaque reinforcement, however, the gallbladder opacified well and appeared radiologically normal. She was then given a fatty meal and the gallbladder contracted promptly to a diameter of 2 cm. Again no calculi were detected. A repeat ultrasound examination, however, demonstrated a 5 mm echogenic focus consistent with a small residual calculus. We suspect this calculus may have been in the gallbladder neck and, thus, not apparent previously. All of her gastrointestinal symptoms had resolved within one week following therapy, and chenodeoxycholic acid therapy was then initiated. At follow-up six weeks after treatment, she had had no further symptoms and her serum aminotransferase and alkaline phosphatase levels had remained normal.

All samples aspirated from the gallbladder during therapy were subsequently analyzed for cholesterol. A total of 13 g of cholesterol was removed, most of which eluted in the first two hours. This amount of cholesterol would be equivalent to 24 spherical 1 cm stones composed of 100% of cholesterol.

EXAMPLE 7

In Vivo Study In A Human Being

A 28-year old Caucasian female underwent a cholecystectomy in February, 1980, for acute cholecystitis, at which time a single 1.3 cm stone was discovered. Intraoperative cholangiography was of good quality and normal, and the patient had an uneventful recovery.

On Jan. 5, 1984, she developed a sudden onset of right upper quadrant pain radiating to her back with associated nausea and vomitting but no fever. The serum alkaline phophatase was 606 u/L ( normal range 76–196 u/L), SGOT 448 u/L (12–30), and total bilirubin 2.6 mg/dl with a direct fraction of 1.9 mg/dl. An ultrasound of the biliary system revealed dilated intrahepatic and extrahepatic ducts.

On Jan. 6, 1984, an abdominal exploration was performed, at which time a large stone was palpated just proximal to the entrance of the cystic duct remnant. At choledochotomy numerous small yellow stones were removed. After vigorous irrigation of the right and left intrahepatic ducts, dozens of additional small stones were removed. On the basis of her normal cholangiogram in 1980, these were felt to be primary duct stones and a side-to-side choledochoduodensotomy was made. The patient's postoperative course was uneventful and she was discharged from the hospital on Jan. 12, 1984.

She continued to have episodic right upper quadrant pain, however, and an endoscopic retrograde cholangiogram on Mar. 1, 1984, revealed a 9 mm stone in the left lateral segment of the left lobe. Basket extraction could not be accomplished for technical reasons and a nasobiliary catheter was placed into the left main hepatic duct to provide access for solvent perfusion. The cholesterol content of her previously removed duct stones was 89% by dry weight, and they dissolved in vitro in MTBE within 3 minutes.

Since MTBE floats on bile, the patient was placed in the right lateral decubitus position to maximize stone-solvent contact. Infusion of 0.5 cc of MTBE through the nasobiliary catheter was then initiated. Every 30 minutes the nasobiliary catheter was aspirated and MTBE was reinfused in gradually increasing volume until a maximum of 2.5 cc was reached. Pain in the mid-abdomen and back was noted by the patient if the injection was too rapid. It was subsequently demonstrated at cholangiography that the catheter had slipped into a small branch of the left duct system, possibly accounting for her intermittent and transient discomfort during infusion. Within 2 to 3 minutes of the first injection, the faint odor of MTBE was detectable on the patient's breath. Treatment was otherwise well tolerated except for a single episode of vomitting of 30 cc of bile-strained fluid which also had an odor of MTBE. After four hours of MTBE instillations (total volume of 7.5 cc) a second cholangiogram was taken which revealed complete disappearance of the stone. A follow-up film the next day confirmed its absence.

Complete blood counts and serum chemistry, including alkaline phosphatase, aminotransferase, amylase, and lipase, showed no abnormalities 4 hours and 24 hours after treatment. There was no evidence of hemolysis and peripheral blood smear and the plasma free hemoglobins remained normal. Both a urinalysis and 24-hour urine for total protein were normal. The patient was discharged on Mar. 3, 1984, feeling well.

These two case reports of Examples 6 and 7 demonstrate that MTBE can be effective in rapidly dissolving cholesterol gallstones in vivo in human beings without serious side effects. Because the gallbladder represents an ideal dissolving chamber which appears to contain the MTBE with little systemic absorption, the use of MTBE for gallbladder stones rather than bile duct stones may represent its greatest potential.

Percutaneous transhepatic puncture of the gallbladder has been performed infrequently in the past and has usually been followed by continuous decompression. Most of those patients, however, have had acute biliary tract inflammation, obstruction, or both. Placement of a soft 5 French (1.7 mm diameter) catheter into the gallbladder using "state-of-the art" hepatobiliary imaging has some risk of leakage of bile, blood, or solvent into the peritoneal cavity of hepatic parenchyma. However, entry of the catheter through the hepatic-gallbladder bed in patients with chronic cholelithiasis without acute inflammation or obstruction should minimize these risks. Furthermore, the presence of a catheter in the gallbladder should permit fragmentation and aspiration or flushing out of the bilirubin debris which may remain after cholesterol stone dissolution and which otherwise might serve as a nidus for stone recurrence.

What is claimed is:

1. A method for dissolving cholesterol calculus comprising contacting the calculus with methyl tertiary-butyl ether.

2. The method of claim 1 wherein the cholesterol calculus of a patient is contacted with methyl tertiary-butyl ether in vivo.

3. The method of claim 2 wherein the cholesterol calculus is selected from the group consisting of biliary duct stones, gallstones in the gallbladder and cholesterol plaque.

4. The method of claim 3 wherein the cholesterol calculus is a gallstone in the gallbladder.

5. The method of claim 1 wherein the cholesterol calculus is contacted with methyl tertiary-butyl ether in the biliary tract of the patient.

6. The method of claim 3 wherein the cholesterol calculus contacted with methyl tertiary-butyl ether is cholesterol plaque.

7. The method of claim 1 wherein in vivo agitation or stirring and aspiration of bile is utilized to facilitate distribution of the methyl tertiary-butyl ether and dissolving of the cholesterol calculus.

8. A method for in vivo dissolving cholesterol calculus in a human patient comprising contacting the calculus with methyl tertiary-butyl ether.

9. The method of claim 8 wherein in vivo agitation or stirring and removal of bile is utilized to facilitate distribution of the methyl tertiary-butyl ether and dissolving of the cholesterol calculus.

10. The method of claim 8 wherein the cholesterol calculus is selected from the group consisting of biliary duct stones, gallstones in the gallbladder and cholesterol plaque.

11. The method of claim 10 wherein the cholesterol calculus is a gallstone in the gallbladder.

12. The method of claim 1 wherein the cholesterol calculus is biliary duct stones.

13. The method of claim 1 wherein the cholesterol calculus is cholesterol plaque.

14. The method of claim 9 wherein bile is continuously or intermittently aspirated from the bile duct or gallbladder and not reinfused.

* * * * *